United States Patent [19]
Parrish et al.

[11] Patent Number: 5,118,624
[45] Date of Patent: Jun. 2, 1992

[54] METHOD FOR THE STIMULATION OF CELL GROWTH AND THE INHIBITION OF CELL PROLIFERATION BY THE UTILIZATION OF SELENODITHIOLS SUCH AS SELENODIGLUTATHIONE

[75] Inventors: Wayne B. Parrish; Darryl N. Willett; Francis A. Kralick, all of Columbus; Gregory N. Orr, Westerville, all of Ohio

[73] Assignee: The Ohio State University, Columbus, Ohio

[21] Appl. No.: 443,608

[22] Filed: Nov. 30, 1989

Related U.S. Application Data

[63] Continuation-in-part of Ser. No. 316,018, Feb. 27, 1989.

[51] Int. Cl.⁵ .......................... C12N 5/00; C12N 9/99
[52] U.S. Cl. .................................. 435/240.2; 435/184
[58] Field of Search .............................. 435/184, 240.2

[56] References Cited

PUBLICATIONS

Vernie et al., "Studies on the Inhibition of Protein Synthesis by Selenodiglutathione", Biochem. J., 180, 1979, pp. 213–218.

Vernie et al., "Inhibition of In Vitro Amino Acid Incorporation by Sodium Selenite", Biochemistry, vol. 13, No. 2, 1974, pp. 337–341.

Vernie et al., Elongation Factor 2 As the Target of the Reaction Product Between Glutathione (GSSeSG) in the Inhibiting of Amino Acid Incorporation In Vitro, Biochim. Biophys. Acta, 414, 1975, pp. 283–292.

Watrach et al., "Inhibition of Human Breast Cancer Cells by Selenium", Cancer Letters, 25, 1984, pp. 41–47.

Poirier et al., "Factors Influencing the Antitumorigenic Properties of Selenium in Mice", J. Nutr., 113, 1983, pp. 2147–2154.

Webber et al., "Inhibitory Effects of Selenium on the Growth of DU-145 Human Prostate Carcinoma Cells In Vitro", Biochem. Biophys. Res. Commun. vol. 130, No. 2, 1985, pp. 603–609.

Medina et al., "Selenium Inhibition on DNA Synthesis in Mouse Mammary Epithelial Cell Line YN-4", Cancer Research, 44, 1984, pp. 4361–4365.

Vendeland et al., "Transport of Selenium as Selenite or Selenomethionine Across Brush-Border Membranes From the Upper Intestines of Rats", The FASEB Journal, vol. 2, No. 6, Abstract 7692, 1988, p. A1621.

Ganther, "Reduction of the Selenotrisulfide Derivative of Glutathione to a Persulfide Analog by Glutathione Reductase", Biochemistry, vol. 10, No. 22, 1971, pp. 4089–4098.

Milner, "Selenium and Carcinogenesis", J. Am. Chem. Soc., 1985, pp. 267–282.

Medina et al., "Uptake and Localization of Selenium-75 in Mammary Epithelial Cell Lines In Vitro", Cancer Letters, 15, 1982, pp. 301–310.

Vernie et al., "Inhibition of the Growth of Malignant Mouse Lymphoid Cells by Selenodiglutathione and Selenodicysteine", Cancer Letters, 14 (3), 1981, pp. 303–308.

Ip, C., "Factors Influencing the Anticarcinogenic Efficacy of Selenium in Dimethylbenz[a]anthracene-Induced Mammary Tumorigenesis in Rats", Cancer Res., 41, 1981, pp. 2683–2686.

Fico et al., "Differential Effects of Selenium on Normal and Neoplastic Canine Mammary Cells", Cancer Res., 46, 1986, pp. 3384–3388.

Primary Examiner—David M. Naff
Assistant Examiner—Mike Meller
Attorney, Agent, or Firm—Frank H. Foster

[57] ABSTRACT

This invention relates to the inhibition of cell proliferation in mammalian host organisms. More particularly the invention relates to the utilization of selenodithiol compositions, particularly selenodiglutathione (GSSeSG) within a narrow concentration range, in which it is both effective as an inhibitor of cancer tumor cell proliferation in mammals, particularly in the prevention of neoplastic cell division in humans, while substantially non toxic outside this narrow range to the treated host organism. The invention also relates to a method for stimulating cellular proliferation at lower concentration of selenodiglutathione.

2 Claims, 7 Drawing Sheets

△ = GSSeSG
○ = SELENOMETHIONINE
□ = SELENITE ($Na_2SeO_3$)

|  | DAY 1 | DAY 8 | DAY 15 | DAY 23 | DAY 30 | DAY 38 | DAY 44 | DAY 51 | DAY 58 | DAY 65 | DAY 72 | DAY 79 |
|---|---|---|---|---|---|---|---|---|---|---|---|---|
| CONTROL |  |  |  |  |  |  |  |  |  |  |  |  |
| # ANIMALS | 50 | 50 | 50 | 50 | 50 | 49 | 49 | 49 | 49 | 49 | 49 | 49 |
| # WITH TUMOR | 0 | 0 | 0 | 0 | 0 | 1 | 4 | 6 | 10 | 15 | 16 |  |
| AVERAGE WEIGHT | 180.0 | 202.8 | 209.9 | 213.0 | 217.7 | 224.8 | 227.0 | 224.2 | 226.0 | 241.9 | 253.8 | 241.1 |
| RETINOL (HPR) |  |  |  |  |  |  |  |  |  |  |  |  |
| # ANIMALS | 10 | 9 | 9 | 9 | 9 | 9 | 9 | 9 | 9 | 9 | 9 | 9 |
| # WITH TUMOR | 0 | 0 | 0 | 0 | 0 | 0 | 0 | 0 | 0 | 0 | 0 |  |
| AVERAGE WEIGHT | 152.0 | 139.4 | 152.0 | 172.0 | 183.4 | 196.8 | 201.3 | 197.8 | 204.3 | 204.3 | 204.3 | 212.9 |
| 1 μg/g GSSeSG+HPR |  |  |  |  |  |  |  |  |  |  |  |  |
| # ANIMALS | 10 | 10 | 10 | 10 | 10 | 10 | 10 | 10 | 9 | 9 | 9 | 9 |
| # WITH TUMOR | 0 | 0 | 0 | 0 | 0 | 0 | 0 | 0 | 0 | 0 | 0 |  |
| AVERAGE WEIGHT | 147.0 | 133.0 | 146.7 | 167.7 | 172.1 | 189.9 | 201.5 | 191.7 | 177.1 | 188.4 | 196.3 | 194.9 |
| 2 μg/g GSSeSG+HPR |  |  |  |  |  |  |  |  |  |  |  |  |
| # ANIMALS | 10 | 10 | 9 | 9 | 7 | 7 | 7 | 7 | 6 | 6 | 5 | 3 |
| # WITH TUMOR | 0 | 0 | 0 | 0 | 0 | 0 | 0 | 0 | 0 | 0 | 0 |  |
| AVERAGE WEIGHT | 152.0 | 139.5 | 147.7 | 172.5 | 175.3 | 185.7 | 201.3 | 192.5 | 200.5 | 201.7 | 208.3 | 209.0 |
| 2 μg/g GSSeSG |  |  |  |  |  |  |  |  |  |  |  |  |
| # ANIMALS | 10 | 10 | 8 | 7 | 7 | 7 | 4 | 4 | 3 | 3 | 1 | 1 |
| # WITH TUMOR | 0 | 0 | 0 | 0 | 0 | 0 | 0 | 0 | 0 | 0 | 0 |  |
| AVERAGE WEIGHT | 175.1 | 189.9 | 200.4 | 215.4 | 216.7 | 219.1 | 234.2 | 215.3 | 233.7 | 239.2 | 224.1 | 235.0 |
| 1 μg/g GSSeSG |  |  |  |  |  |  |  |  |  |  |  |  |
| # ANIMALS | 10 | 10 | 10 | 10 | 10 | 10 | 10 | 9 | 9 | 9 | 7 | 7 |
| # WITH TUMOR | 0 | 0 | 0 | 0 | 0 | 1 | 1 | 1 | 1 | 1 | 1 |  |
| AVERAGE WEIGHT | 182.0 | 194.6 | 202.5 | 215.8 | 217.8 | 221.9 | 215.7 | 221.8 | 219.3 | 220.1 | 222.8 | 222.5 |

FIG 3

METHOD FOR THE STIMULATION OF CELL GROWTH AND THE INHIBITION OF CELL PROLIFERATION BY THE UTILIZATION OF SELENODITHIOLS SUCH AS SELENODIGLUTATHIONE

This invention is a continuation in part of the patent application filed on Feb. 27, 1989 with U.S. Ser. No. 07/316,018 titled "Method For The Inhibition Of Cancer Cell Proliferation By The Utilization Of Selenodithiols Such As Selenodiglutathione".

TECHNICAL FIELD

This invention relates to medical treatments for the inhibition of cell proliferation, including but not limited to, cancer cell proliferation in mammalian host organisms. This invention also relates to medical treatments for the stimulation or enhancement of cell proliferation.

BACKGROUND ART

Cancer is one of the most significant causes of death in the world, accounting for approximately 20% of all deaths in humans. The disease, as is commonly well known, can effect persons of all ages, background, and socio-economic status.

There have been a variety of attempts in the prior art which indicate that selenium compounds can exhibit both anticarcinogenic and antimutagenic potential in both in vitro and in vivo systems.

An article by Vernie et al., in *Biochem Journal* (1979), 180, 213-218 entitled "Studies on the Inhibition of Protein Synthesis by Selenodiglutathione" discloses that GSSeSG is substantially more effective in inhibiting protein synthesis than sodium selenite ($Na_2SeO_3$) or oxidized glutathione; more particularly, in a cell-free system derived solely from rats, GSSeSG blocks amino acid incorporation through the inactivation of elongation factor 2 (EF-2). Also, the particular concentrations of GSSeSG utilized (4 μg/ml) are significantly different than the concentrations utilized by applicants. Additionally, neither the binding of aminoacyltRNA to the ribosomes by elongation factor 1, nor the peptidyltransferase reaction, nor the ribosomes per se were affected. The reference further discloses (p218) that the inhibition of protein synthesis of cells in tissue culture opens a new perspective on counteracting tumor cells with selenium-type compounds of the general formula RSSeSR. However, the biphasic effect of the present invention is not taught in the reference.

Another, article by Vernie et al. in *Biochemistry*, Volume 13, number 2, pgs. 337-391, 1974 entitled "Inhibition of in vitro amino acid incorporation by sodium selenite" discloses that selenite concentrations of $1.1 \times 10^{-5}$M can inhibit EF-2, and the author's earlier work, Vernie et al., *Biochem. Biophys. Acta.*, 414, 283-292 (1975) discloses that EF-2 is the target of the reaction product between $Na_2SeO_3$ and glutathione in the inhibiting of amino acid incorporation in vitro. However, the biphasic effect of the present invention is not taught in the reference.

An article by A. M. Watrach et al., in *Cancer Letters*, 25 (1984) 41-47, entitled "Inhibition of Human Breast Cancer Cells by Selenium" discloses that the parenteral administration of sodium selenite ($Na_2SeO_3$) completely inhibits the development of cancerous tumors in mice. The article further indicates that selenium can be transported by the host from a distant administration site to the site of the tumor, where it accumulates within and exerts its inhibiting effect upon cancer cell mitosis. However, the biphasic effect of the present invention is not taught in the reference.

An article by Poirier and Milner, *J. Nutr.*, (1983) entitled "Factors Influencing the Antitumorigenic Properties of Selenium" teaches that the intermediate products of selenium metabolism, such as GSSeSG, are as effective as selenite. However, the article does not disclose the non toxicity of GSSeSG, that GSSeSG is not as mutagenic as $Na_2SeO_3$, nor the biphasic effect of the present invention.

An article by Webber et al., *BioChemical and Biophysical Research Communications*, Vol. 130, No. 2, (1985), 603-609, "Inhibitory Effects of Selenium on the Growth of DU-145 Human Prostate Carcinoma Cells In Vitro" discloses that selenium, when administered as sodium selenite, inhibits the growth of human prostate carcinoma cells in vitro, as well as in other types of cancer cells. The reference further indicates that selenium can inhibit both the initiation and promotion stages of carcinogenesis (page 607) and that selenium inhibits DNA synthesis, as reported by Medina et al., (1984) *Cancer Research*, 44, 4361-4365. However, the biphasic effect of the present invention is not taught in the reference.

Vendeland et al, "Transport of Selenium as Selenite or Selenomethionine Across Brush-Border Membranes From the Upper Intestines of Rats", *The FASEB Journal*, Vol. 2, No. 6, Abstract 7692, 1988, p. A1621 (Vendeland et al.), disclose an abstract entitled the "Transport of Selenium As Selenite Or Selenomethionine Across Brush-Bordered Membranes From the Upper Intestines of Rats".

The GSSeSG utilized in the present invention was prepared by modifying a variation in the method of Ganther, reported in *Biochemistry*, 10:#22, 4089-4098, and improved by Vernie et al., Biochem. Journal (1979), 180-218, page 213.

An article by Milner entitled "Selenium and Carcinogenesis", (1985) *American Chemical Society*, 267-282 discloses that the anticarcinogenic property of selenium does not appear to be mediated through its association with glutathione peroxidase activity. Selenium is further disclosed as being effective in inhibiting the proliferation of neoplastic cells, and that GSSeSG, or other intermediate compositions which occur during selenium metabolism, are suggested as responsible for the antitumorigenic properties of this element. The diagram on page 278 describes a flow diagram of selenium metabolism which proceeds through GSSeSG.

An article by Medina et al., *Cancer Letters*, 15 (1982) 301-310, entitled "Uptake and Localization of Selenium-75 in Mammary Epithelial Cell Lines In Vitro" discloses that selenium can inhibit the growth potential of chemical carcinogen-induced tumorigenesis in mice.

A later article by Vernie et al., (1981) *Cancer Letters* (Shannon, Irel) 14(3), 303-313 entitled "Inhibition of the Growth of Malignant Mouse Lymphoid Cells by Selenodiglutathione and Selenodicysteine" discloses that intraperitoneal injections of GSSeSG or selenodicysteine in mice, which had been previously inoculated with tumor cells, inhibited the tumor growth and increased the life span of the animals as compared with the untreated control mice.

An article by Clement Ip, "Factors influencing the anticarcinogenic efficacy of selenium in DMBA-induced mammary tumorigenesis in rats"; *Cancer Re-* search, 41:2683-2686 (1981) teaches that dosages of Na$_2$SeO$_3$ given to rats on low fat diets decrease tumorigenesis, but high fat fed animals did not respond as favorably. The results suggested that selenium has no effect on the proliferation of malignant vs. benign lesions. However, the reference does not teach the use of selenodithiols nor the biphasic effect of the present invention.

An article by Fico et al., "Differential effects of Se on normal and neoplastic canine mammary cells", *Cancer Res.* 46, 3384-3388 (1986) describes the differential effects of Se on normal and neoplastic canine mammary cells.

An article by Khalil et al entitled "5-Bromodeoxyuridine- and N-Methyl-N-Nitrosourea- Induced Sister Chromatid Exchanges Correlate With Reduced Survival Not Cell Kinetics Of Cultured Human Lymphocytes" disclosed that Sister Chromatid Exchange techniques can be utilized to determine the non-mutagenicity of GSSeSG as compared to other forms of selenium.

Although it is clear that the prior art has attempted a variety of processes which have shown a certain amount of effectiveness in the treatment of carcinogenic cells through the utilization of selenium-containing compounds, these efforts have been unable to effectively destroy cancer cells without also damaging the treated host organism, and do not show a biphasic effect of selenodithiols administered to cells.

SUMMARY OF THE INVENTION

Accordingly, it is an object of the invention to provide both a process and also compositions for the utilization of selenium containing compounds which create a toxic crisis in cells, including but not limited to, cancerous cells, while also providing a non toxic environment for the normal host cells.

It is another object of the invention to provide a process which utilizes a small genus of selenodithiols, and particularly GSSeSG, to effectively inhibit tumor cell proliferation in both humans and other animals.

Another object of the present invention is to provide an immunosuppressive therapy wherein mammalian immune system is suppressed by the administration to the mammalian host of an organo-selenium compound.

Yet another object of the present invention is an autoimmune suppressive therapy wherein mammalian autoimmune system is suppressed by the administration to the mammalian host of an organo-selenium compound.

Still another object of the present invention is the stimulation of cell growth by the administration of specific amounts of an organo-selenium compound. This embodiment of the biphasic effect of the present invention can be useful for the development of cell growth medium and also for the proliferation of epithelial cell for the treatment of skin wounds, such as commonly found in burn victims.

The present invention is further related to a method for the treatment of individuals displaying abnormally low levels of dopamine by the stimulation of new cell growth within the substantia nigra region of the brain. In this manner, the dopamine levels naturally produced by the brain are increased as a result of the biphasic effect of the invention. Increased dopamine levels in the brain has been found to be helpful in the medical treatment of Parkinsonism. Thus the present invention is also directed to a method for the treatment of Parkinsonism by the administration to an afflicted individual of an effective amount of an organo-selenium compound to the brain.

The present invention is further directed to the treatment of fungal infected cells and virally infected cells, wherein the treatment comprises administering to the cells an amount of an organo-selenium compound sufficient to stimulate a biphasic immuno-regulatory proliferation and the destruction of the infectious agent without toxic side effects to the cells or to the host organism.

By the present invention is also provided a biphasic method for the inhibition of the elongation factor 2 (EF-2) in eucaryotic cells by the administration to the cells of an organo-selenium compound in an amount sufficient to inhibit the protein synthesis.

The invention further comprises a method for the inhibition of cell proliferation in a mammal, comprising administering a pharmaceutically effective amount of a selenodithiol or its pharmaceutically acceptable salts for a sufficient time to the mammal. In particular, the selenodithiol, GSSeSG, when present in concentrations ranging from about $10^{-6}$M to about $10^{-5}$M effectively inhibits cancer cell proliferation in the treated host mammal without significant toxicity to the non-cancer cells of the host mammal. "Administration" as used herein includes but is not limited to direct injection, cannulation, inhalation, enema, transdermal application, subdermal implantation, subdermal pump, oral ingestion of pill form or throat lozenge, or an equivalent application to an area to be treated. Other methods of conventional administration of medicaments will also be effective herein and these are known to those skilled in the art.

By "biphasic effect" herein is meant the combination of enhanced cellular activity in cells treated with the selenodithiol at concentrations below about $10^{-6}$M and the decreased cellular activity and/or death in cells treated with the selenodithiol at concentrations above about $10^{-6}$M.

BRIEF DESCRIPTION OF DRAWINGS

Various other objects, features and attendant advantages of the present invention will be more fully appreciated when considered in connection with the accompanying drawings wherein:

FIG. 3 provides the results obtained from treating each of five groups of rats, which were previously inoculated with a chemical carcinogen and were then subsequently tested with different dosages of cancer treating agents, including GSSeSG, and further comparing the results with a control group of cancer infected but untreated rats.

Figure 1:
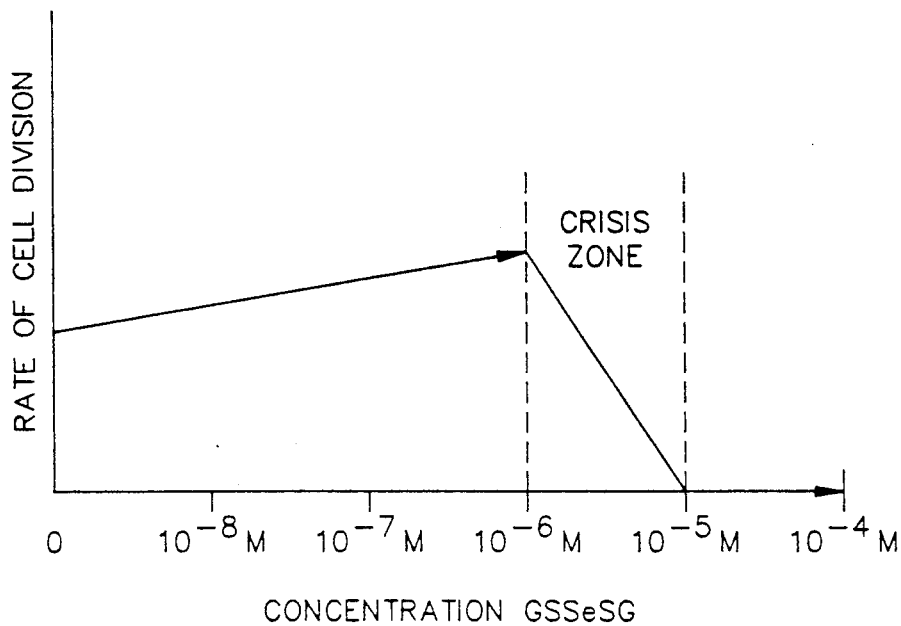
FIG. 1 provides a plot measuring neoplastic cell division or cell protein synthesis as a function of the concentration of the preferred selenodithiol, GSSeSG.

In describing the preferred embodiment of the invention, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION

The invention, in particular, relates to the utilization of a small genus of selenodithiol compounds which includes selenodimethionine and selenodicysteine and particularly selenodiglutathione (GSSeSG), which are capable of preventing cells, including cancer cells, from proliferating while being substantially non-toxic to the mammalian host organism being treated, including humans. This surprising discovery has been demonstrated by both extensive in vivo rat data as well as in vitro experiments on human neoplastic and non-neoplastic cells, including among others, fibroblasts and keratinocytes.

More particularly, a surprising biphasic effect can be seen with increasing concentrations of GSSeSG. The second stage results in a so-called "crisis zone" in which the growth of the cells, including for example cancer cells, is substantially terminated within a particularly narrow range of GSSeSG concentrations, and, surprisingly, without significant damage to the host organism being treated. More particularly, at concentrations less than the critical range, i.e., less than about $10^{-6}M$, the proliferation of cells actually increases while being treated with GSSeSG, but within this narrow, i.e., crisis zone, range the target cells are substantially eliminated, while the surrounding non target cells are substantially unharmed.

The present invention provides a biphasic method for the inhibition of elongation factor 2 (EF-2) by the administration of an organo-selenium compound in eucaryotic cells in an amount sufficient to inhibit the protein synthesis. Polypeptide chains in proteins are lengthened by covalent attachment of successive amino acid units, each carried to the ribosome and put into its proper position by its corresponding t-RNA, which is base-paired to its corresponding codon in the messenger RNA. Elongation is promoted by cystosolic proteins called elongation factors. It is known that toxins such as diphtheria toxin can catalyze the transfer of the ADP-ribosyl moiety of nicotinamide adenine dinucleotide (AND) onto the elongation factor 2 (EF-2), thereby inhibiting protein synthesis in eucaryotic cells. The invention relates to the fact that selenodithiols which are selected from a small class of compounds, and particularly GSSeSG, appear to inhibit the EF-2 by direct binding.

The inventors believe but do not wish to be limited to the theory that the role of the EF-2 in the cell is to drive the synthesis of the protein being formed in the desired direction through the two initiation sites, A and P, present on the ribosomes. The EF-2 governs the particular elongation of the protein to be formed in that the mRNA, selects the precise order of the amino acids to proceed through the A and P sites to form the resulting protein.

The invention particularly relates to the use of GSSeSG and its pharmaceutically acceptable salts, the structure of GSSeSG being set forth below:

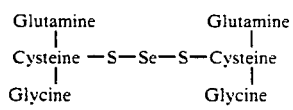

where S is a sulfur atom, and Se is a selenium atom.

It is believed that GSSeSG inhibits the EF-2 factor through the creation of a biphasic effect of selenium on the cellular growth of the cancer cells. GSSeSG is, as seen above, a hexapeptide made from glutamine, cysteine and glycine, in which the cysteine moiety contains an —SH group which, it is hypothesized, aligns with the selenium on a corresponding glutathione molecule to form a linear structure, although applicants do not wish to be bound by theory with respect to a particular mechanism of operation. In the broadest embodiment, it is believed that any cell containing EF-2 can be inhibited by GSSeSG administered at levels of $10^{-6}M$ to $10^{-5}M$, and any cell containing EF-2 can be stimulated to grow by the GSSeSG administered at levels of $10^{-6}M$ to $10^{-8}M$; thus, the compositions of the invention are effective in all eucaryotic cells, including but not limited to, mammalian neoplasms and chemically induced as well as naturally induced cancerous cells.

It is interesting to compare the structure of GSSeSG with glutathione in its reduced form, the structure of which is shown below,

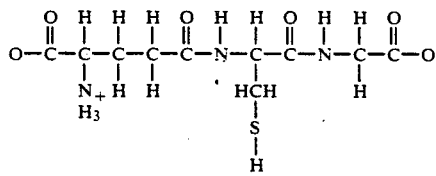

wherein the cysteine moiety contains the sulfur atom. It has been hypothesized that selenium can effectively substitute itself for the hydrogen atom bonded to the sulfurs, although as stated, supra, applicants do not wish to be bound by theory.

It should be noted that the R groups in the genus of selenodithiols can include substantially all organic compounds which contain a thiol group, such as cysteine, methionine and the like. Consequently, one of the advantages of the resulting compounds includes an ability to carefully control both the resulting water and fat solubility of the selenium containing compounds, as well as molecular weight, dipole moment, and other characteristics important for cell membrane permeation.

Major problems with currently available cancer therapy which need to be addressed are the inability to obtain sufficient quantities of chemotherapeutics at the tumor site, problems of nonspecific toxicity, and a loss of toxicity associated with the inefficient uptake and processing of chemotherapeutics. The use of hybridoma technology has provided the solution to the first problem area in which magic bullets of tumor specific antibodies conjugated to chemotherapeutic agents aid in localizing the drug to the site of the tumor, thus diminishing toxic effects on normal tissue. To date, the majority of the immunotoxin studies have concentrated on the use of two readily available toxins: ricin, a plant lectin, and diphtheria toxin produced from bacterial cultures which are commercially available. Typically, these and other such immunotoxin complexes bind to the cell surface receptor and enter the cytoplasm following translocation across the membrane, in a manner well known to the art. Once inside, the toxin inhibits protein synthesis through a particular enzymatic reaction.

Accordingly, there currently exists in the art a need to overcome the aforementioned difficulties and provide an immunotoxin therapy which is not only effective against cancer, but is also nontoxic to the host organism being treated. The present invention, using a composition such as GSSeSG alone or in combination with a suitable monoclonal antibody, is believed to overcome this problem.

The invention therefore relates to a process to suppress mammalian immune system and autoimmune system by the administration to the mammalian host of a sufficient amount of an organo-selenium compound. The organo-selenium compounds can include selenodithiols, such as selenodimethionine, selenodicysteine, and, preferably, selenodiglutathione (GSSeSG). According to the present invention, the administration to the mammalian host of the selenodithiol results in the inhibition of protein synthesis in rapidly dividing immune cells by the mechanism of EF-2 inhibition. This has a down regulating effect on the autoimmune process. It is believed that an effective amount of selenodithiol in the suppression of mammalian immune and autoimmune systems is an amount in excess of $10^{-6}M$ and preferably not exceeding $10^{-5}M$ per dose.

In this manner is provided a method to suppress mammalian immune system by the administration to a mammalian host of an effective amount of a selenodithiol or its pharmaceutically acceptable salt. In this manner is also provided a method to suppress mammalian autoimmune system by the administration to a mammalian host of an effective amount of a selenodithiol or its pharmaceutically acceptable salt.

An important consequence of the proliferative property of injected selenodiglutathione in concentrations below the critical range is the upregulation of protein synthesis resulting in the increased expression of antigenic proteins on the cell membrane. This upregulation is a critical component in the process of localizing cancerous lesions for the effective use of radio-immuno therapy, gamma scans and radio-immuno guided surgery. The compound alpha-interferon is now being tested for this upregulation property with some success. This role of selenium is felt to be indirectly responsible for the effective localization and treatment of a variety of cancers by enhancing the effect of the magic bullet concept of radio-immunology. This property can be used in addition to the cytotoxic effect which can be linked directly to the antibody in order to inhibit protein synthesis of a cancer cell.

Furthermore, the present invention is also directed to a method for the treatment of autoimmune disease comprising administering to a mammalian host afflicted with autoimmune disease an effective amount of a selenodithiol, such as selenodimethionine, selenodicysteine, or preferably selenodiglutathione. An autoimmune disease is one in which the body attacks its own tissues, failing to differentiate between what is foreign and what is not. Rheumatoid arthritis and lupus, or systemic lupus erythematosus, for example, are autoimmune, inflammatory diseases of connective tissue. By the present invention, a selenodithiol can be administered to a mammalian host exhibiting autoimmune disease whereby the autoimmune system is suppressed, thus allowing the healthy tissue to survive. A preferred level of selenodithiol useful for treating autoimmune disease is an amount ranging from about $10^{-6}M$ to about $10^{-5}M$. The present invention is also directed to the treatment of fungal infections, protozoan infections, and virally infected cells by the administration of an effective amount of a selenodithiol to the infected cells. A preferred level of selenodithiol useful for treating fungal infections is an amount ranging from about $10^{-6}M$ to about $10^{-5}M$. A preferred level of selenodithiol useful for treating virally infected cells is an amount ranging from about $10^{-6}M$ to about $10^{-5}M$. The treatment of fungal infections and virally infected cells can be achieved according to the present invention by means of inhibition of EF-2 which is possessed by both fungal and virally infected host cells. It is believed that protozoan infection of a mammalian host can also be reduced or eliminated by administration to the mammal of an amount of selenodithiol. Thus, protozoan infections including pin worms, whip worms, tape worms, heart worms, amoba, and the like can be treated by the present invention.

MATERIALS AND GENERAL PROCEDURES

Preparation Of GSSeSG

GSSeSG was synthesized by utilizing a modification of the method of Ganther, reported supra. The purification column was prepared by first preparing a solution containing 32.8 g of NaAc, 9.48 g NiCl$_2$, and 3.8 liters of double distilled H$_2$O. The resulting solution was adjusted to a pH of 4.7 and then added to 2000 grams of the cationic resin, Dowex-50-X400, so as to obtain a moderately thick slurry. The resulting resin slurry was poured into a 130 cm long, 44 mm inner diameter column maintained at a temperature of 4° C., and the resin was allowed to settle in the column, with the stopcock being kept open so that only a slow drip of solution was able to exit the column. Then, a pump was connected to the base of the column to draw the eluent out of the column and into a spectrophotometer in order to determine exactly when the formed GSSeSG could be collected.

GSSeSG was prepared by forming a solution of 500 mg of reduced glutathione obtained from Gallard Schlesinger, Carl Place, N.Y. and 10 ml of 0.1N HCl.

The resulting solution was kept on ice, as was a second solution comprising 90 mg of $Na_2SeO_3$ and 5 ml of 0.1N HCl, which was also prepared. Upon completion, the glutathione solution was poured into the $Na_2SeO_3$ solution and mixed. The resulting solution was allowed to sit for 15 minutes, whereupon the pH was adjusted to 4.5 by the addition of 2M NaAc, and the resulting solution was poured into the purification column.

GSSeSG was purified and concentrated by first removing the nickel from the resin slurry solution of NaAc, $NiCl_2$, $H_2O$, and resin prepared above by adding concentrated NaOH, mixing and then aspirating off the nickel. Upon completion, 0.1N formic acid was added to the solution until the pH of the resin solution was about 2.6, and the resulting resin solution was poured into the aforementioned small purification column. Again, the resin was allowed to settle with the stopcock open until a slow drip of solution was seen exiting the column. The pump was then attached to the base of the column and hooked up to the spectrophotometer as before. GSSeSG, which had been adjusted to a pH of 3.0 by addition of 5N HCl, was allowed to slowly drip into the top of the column, being assisted by the pump. At the point where only about a quarter inch of GSSeSG was left on the top of the column, 0.1N formic acid was slowly poured into the top of the column until several volumes of formic acid had passed through and washed the purification column. Upon completion, 0.1M Ammonium acetate, having a pH of 5.5, was added by slowly dripping into the top of the column. At the point when the pH of the solution in the column attains a value of 3.3, pure GSSeSG can be produced, ending at a pH of about 4.2. The resulting product was frozen at $-20°$ C. for storage for later usage.

Although not essential to the procedure, assuming it is desired to reuse the column to produce GSSeSG, it is preferred to put the resin in a beaker of 0.1N NaAc, 0.01N NaOH and water until ready to use again, at which time the excess nickel must be removed by swirling, aspirating and adjusting to a pH of 4.7.

Cell Culture Assay

The cell culture assay is a method for measuring what concentration of the selenodithiol treating agent will inhibit neoplastic cell division or protein synthesis, and thus cause the death of the neoplastic cells. The particular assay technique is a modification of that described by Mosmann, Jour. of Immunol. Meth. 65:55–63, (1983). The cell lines used for the in vitro assay are:

| A549 | lung adenocarcinoma |
|---|---|
| HT29 | colon adenocarcinoma |
| TE 671 | medulloblastoma |
| RPMI 7951 | melanoma |
| MCF 7 | breast adenocarcinoma |
| 12-18 | glioma |
| CI | normal fibroblasts (non-neoplastic strain) |
| Keratinocytes | normal keratinocytes from foreskin (non-neoplastic strain) |

The plating density of each cell type used in the assay is set forth below:

| A549 | 15,000 cells/well |
|---|---|
| HT29 | 1,000 cells/well |
| TE 671 | 1,000 cells/well |
| RPMI 7951 | 30,000 cells/well |
| MCF 7 | 15,000 cells/well |
| 12-18 | 7,500 cells/well |
| CI | 30,000 cells/well |
| keratinocytes | 15,000 cells/well |

The procedure followed involved adding for each cell type 200 μl of the cell suspension at the concentration determined above, to each well of a 96-well plate. The plates were allowed to incubate for 24 hours at 37° C. and humidified in the presence of a 5% $CO_2$ atmosphere, whereupon 20 μl of GSSeSG concentrations ranging from $10^{-8}M$ to $10^{-4}M$ were added to the wells located on the plate. Phosphate buffered saline and a variety of concentrations of adriamycin were utilized as controls. The resulting plates were incubated for six days at 37° C., humidified in a 5% $CO_2$ atmosphere and on the final day of the assay, 20 microliters were added to each well of MTT [3-(4,5-dimethylthiazol-2-yl)-2,5-diphenyl tetrazolium bromide], obtained from Sigma Cat #M2128. The MTT is prepared by combining 5 mg/ml of a phosphate buffered saline (PBS) solution. The resulting plates were allowed to incubate for 4 hours at 37° C., whereupon the contents of the plate were dumped and blotted dry on a diaper and 100 microliters of DMSO were added to each well in order to dissolve the formazan crystals which were formed through the reduction of MTT in the presence of the active mitochondria within the cell. Upon completion, the optical density of each well was read on an elisa plate reader set at 570 nm (test sample) and 630 nm (for reference).

The results obtained disclose that if concentrations less than about $10^{-6}M$ of GSSeSG were utilized, a purple solution was obtained, which indicates that a concentration of GSSeSG present will enable the neoplastic cells to survive suggested by the ability of active mitochondria to reduce the yellow MTT solution to a purple formagen solution. However, if concentrations of at least about $10^{-5}M$ of GSSeSG are utilized, the purple solution is not obtained, thus indicating that the concentration of GSSeSG is inhibiting the neoplastic cell division, or protein synthesis, referred to above.

The results set forth above can be more easily seen by viewing FIG. 1 in which a plot of neoplastic cell division or cell protein synthesis is described as a function of the concentration of the preferred selenodithiol GSSeSG. As the graph clearly illustrates, the crisis zone is located between a concentration of $10^{-6}M$ and $10^{-5}M$, wherein the formerly increasing rate of cell division is substantially reduced to zero. In this crisis zone range of concentrations, all of the human cancer cells listed above, when treated with GSSeSG within the cited concentration range, are essentially prevented from dividing.

An additional advantage not readily apparent from the results of the Figure is that as one increases the concentration of the selenodithiol, e.g., GSSeSG, up to about $10^{-6}M$, the neoplastic cell division actually increases, thus providing a method to grow cells in a suitable culture. Such a technique is particularly useful if it is desired to grow, e.g., epithelial cells rapidly in order to transplant them to a patient. In addition, this technique can be used in the development of cell growth medium or culture medium. As can be seen, growing the aforementioned cells in low concentrations of GSSeSG increases the rate of growth so as to enable one to rapidly obtain the desired amount of tissue for, e.g., in the case of a burn victim, or a tissue implant or expedite wound healing. A further use for such a growth factor would be to stimulate the immune system of immuno-compromised individuals.

Thus the present invention relates to the administration to cells of skin tissue an amount of a selenodithiol sufficient to stimulate proliferation of said cells of skin tissue. The selenodithiol can be selenodimethionine, selenodicysteine, or selenodiglutathione. The selenodithiol can be administered directly to or near the site of a skin wound or to healthy skin tissue which is thereafter transplanted to or near the site of a skin wound. Alternatively, the cells of skin tissue can be treated in vitro with the selenodithiol and then implanted into or near the site of the skin wound. The treatment of skin cells can be within the layers of the epidermis including the stratum basale, stratum spinosum, stratum granulosum, stratum lucidum, and stratum cornum. Skin wounds can also be treated according to the present invention by the administration of selenodithiol to the dermis part of the skin, including the papillary layer and the reticular layer. Skin wounds can also be treated according to the present invention by the administration of selenodithiol to the subcutaneous layer of the skin beneath the dermis. Epithelial cells which will respond to proliferation and growth stimulation upon exposure to a sufficient amount of selenodithiol are believed to include stratified squamous cells, stratified cuboidal cells, stratified columnar cells, stratified transitional cells, simple squamous cells, simple cuboidal cells, and simple columnar cells. A preferred level of selenodithiol useful for promoting the proliferation and growth stimulation of skin cells is an amount less than about $10^{-6}M$.

The present invention also provides a method for the treatment of individuals with Parkinsonism disease. Parkinson's disease is a degenerative and progressive disorder exhibiting muscular tremor and akinesia, which has been associated with a loss of dopamine in the brain. Dopamine is 3,4-dihydroxyphenylethylamine and is not easily transported into the brain because of the so-called blood-brain barrier. Thus conventional treatment has used dopamine's immediate metabolic precursor, Dopa (dihydroxyphenylalanine), which is readily taken up by the brain. The treatment for Parkinsonism of the present invention includes the administration to an afflicted individual of an effective amount of an organo-selenium compound, preferably a selenodithiol, such as selenodiglutathione, selenodimethionine, and selenodicysteine. It is believed that an effective amount of selenodiglutathione in the treatment of Parkinsonism is an amount in excess of $10^{-8}M$ per dose but preferably not exceeding $10^{-6}M$ per dose. The treatment method of the present invention is effective for Parkinson's disease, it is believed, by stimulating the growth or proliferation of certain cells within the brain, apparently the substantia nigra portion of the brain, or enhancing protein synthesis of dopamine which results in the increased production of dopamine. GSSeSG may be used to stimulate the substantia nigra area of the brain responsible for the production of dopamine by increasing the number of cells performing that function or enhancing the existing cell's protein synthesis mechanism to produce increased levels of this neurotransmitter. Currently surgery is being done with limited success in transplanting portions of the adrenal medulla to the substantia nigra portion of the brain. During this process, it is believed that GSSeSG could be used to aid in the growth and proliferation of this brain area to provide increased success in these patients.

Conventional treatment for regression in certain disseminated neoplastic conditions has included cytotoxic anthracycline antibiotics isolated from various cultures. Adriamycin is often used in the treatment of conditions such as acute lymphoblastic leukemia, acute myeloblastic leukemia, Wilm's tumor, neuroblastoma, soft tissue and bone sarcomas, breast carcinoma, ovarian carcinoma, transitional cell bladder carcinoma, thyroid carcinoma, lymphomas of both Hodgkin and non-Hodgkin types and bronchogenic carcinoma. However, adriamycin is contraindicated where pre-existing heart disease is present or where adriamycin has been used extensively with the patient before. One reason for this contraindication is the possibility of cardiac toxicity which has been associated with adriamycin. It is believed that adriamycin causes the formation of free radicals in the tissue of the host animal which can damage the tissue. Such free radical-induced tissue damage can lead to heart disease. By the present invention, adriamycin may be administered in conjunction with, although not necessarily admixed with, an amount of a source of selenite such as selenodithiol sufficient to act as a free radical scavenger, whereby free radicals produced by the adriamycin are quickly absorbed by the glutathione peroxidase produced and rendered non-reactive. This results in the protection of healthy heart tissue from free radical damage. Furthermore, combined therapy of adriamycin and a source of selenite such as selenodiglutathione allow for reduced amounts of both agents to be utilized, possibly eliminating the unwanted side effects of each when given individually while providing efficient antineoplastic potential.

In addition to scavenging the free radicals, the selenodithiol, or the peroxidase produced therefrom, is effective against many cancerous cells. The invention discloses that a small class of selenodithiols including selenodimethionine, selenodicysteine and, most particularly, GSSeSG, can alter the growth of cancerous mammalian and human cells when appropriate dosages having a very narrow range of effective concentrations are applied. In particular, at concentrations between about $10^{-6}M$ and about $10^{-5}M$, GSSeSG substantially inhibits proliferation of such neoplastic cells. Indeed at these concentrations all growth is inhibited. When a toxic dose ($10^{-5}M$) is administered to the neoplasm, the radial diffusion of the "dose" becomes less toxic at distances until (its) concentration nears the concentration of $10^{-6}M$ at which time the normal surrounding tissue is unharmed.

Figure 2:
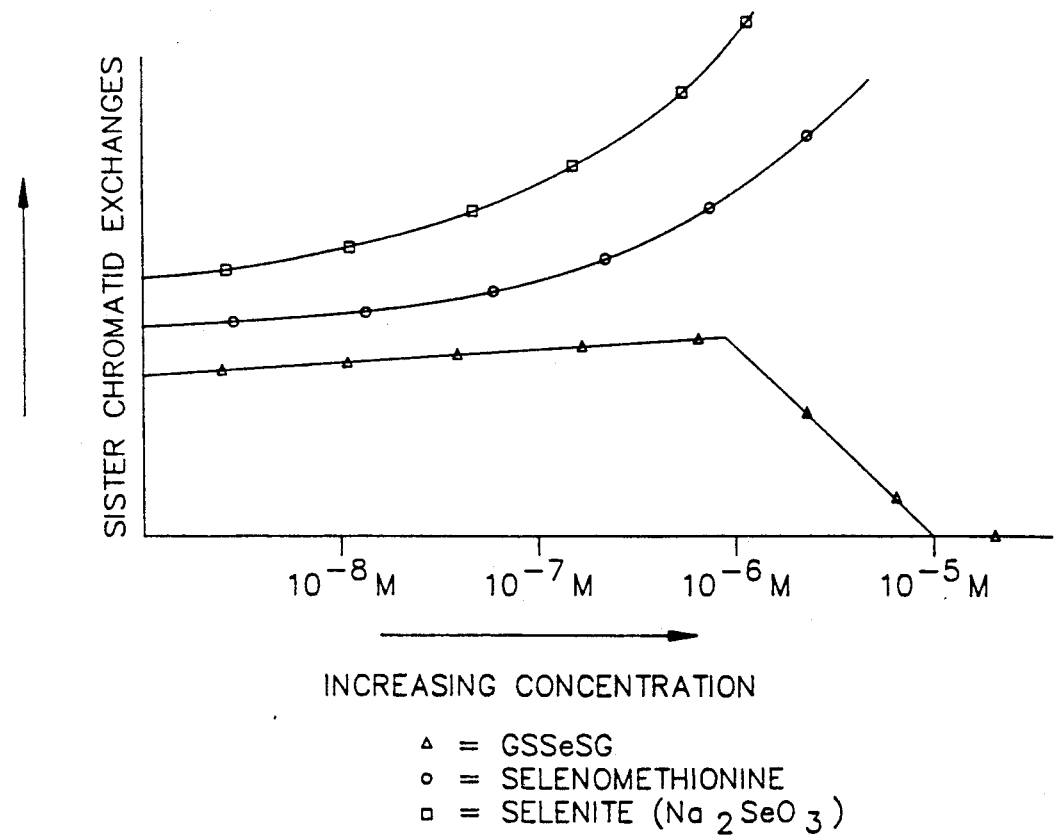
FIG. 2 provides a plot measuring the mutagenicity of three selenium based agents as a function of the concentration of each specific agent, one of which is GSSeSG.
Figure 4:
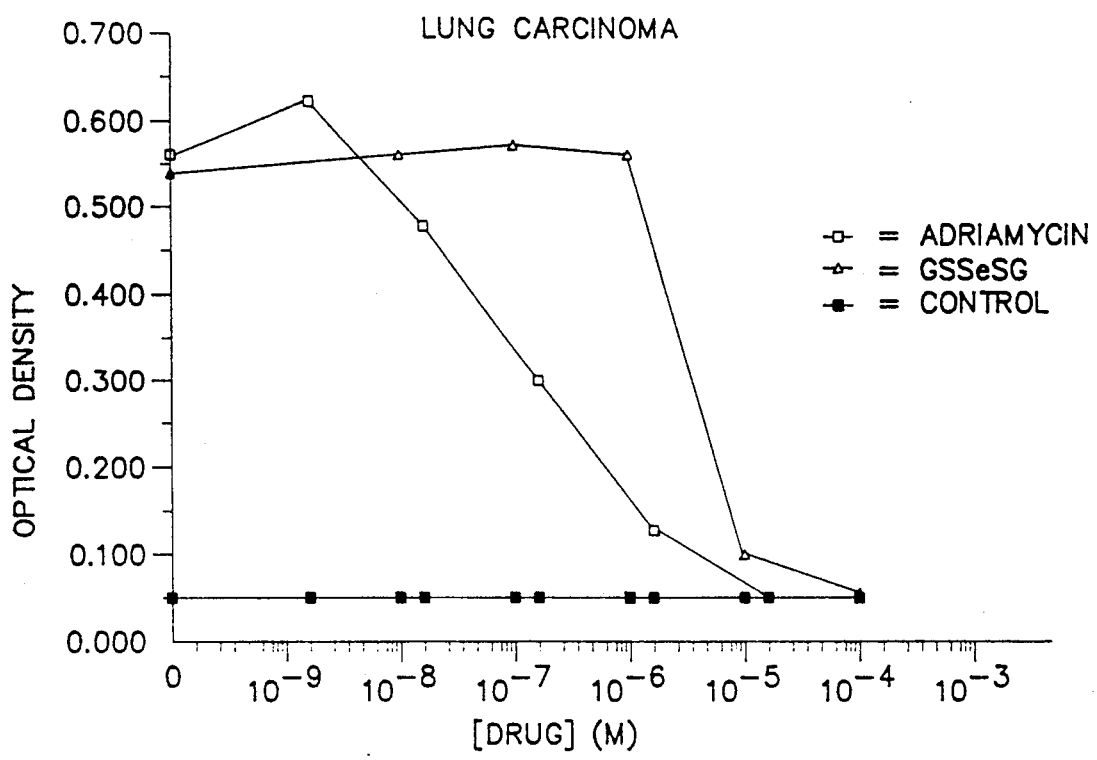
FIG. 4 provides a comparison of the effects at increasing concentrations of adriamycin and GSSeSG as measured by variations in optical density of the cell solution of lung carcinoma.
Figure 5:
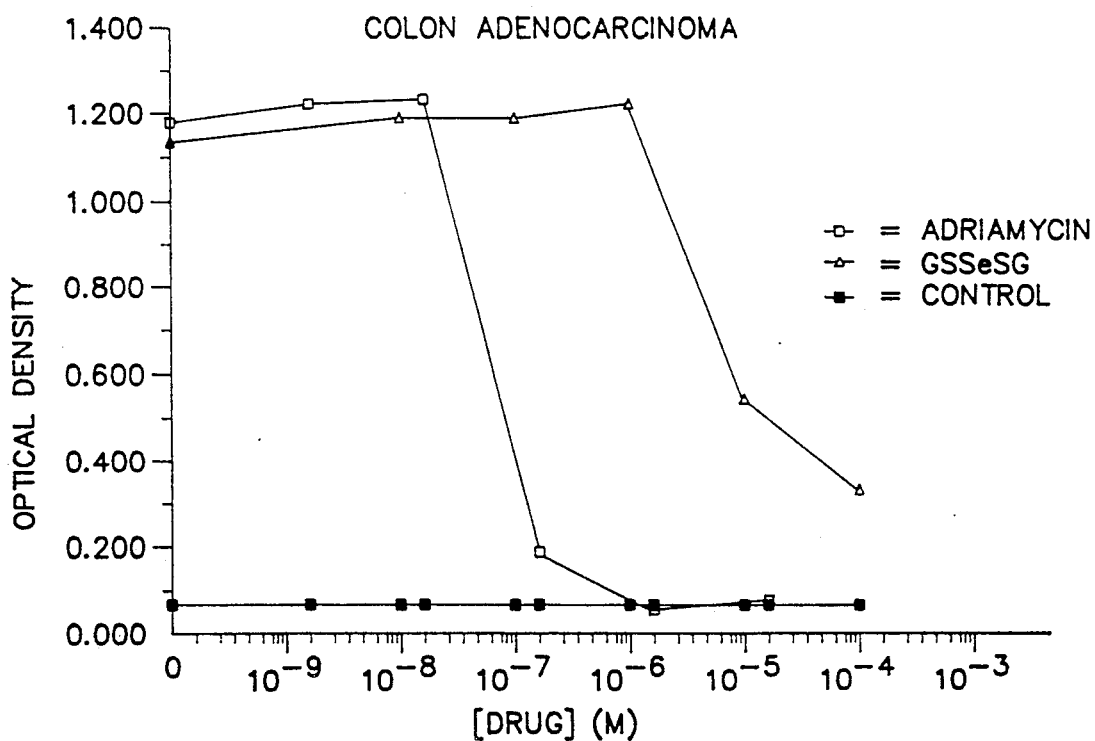
FIG. 5 provides a comparison of the effects at increasing concentrations of adriamycin and GSSeSG as measured by variations in optical density of the cell solution of colon adenocarcinoma.
Figure 6:
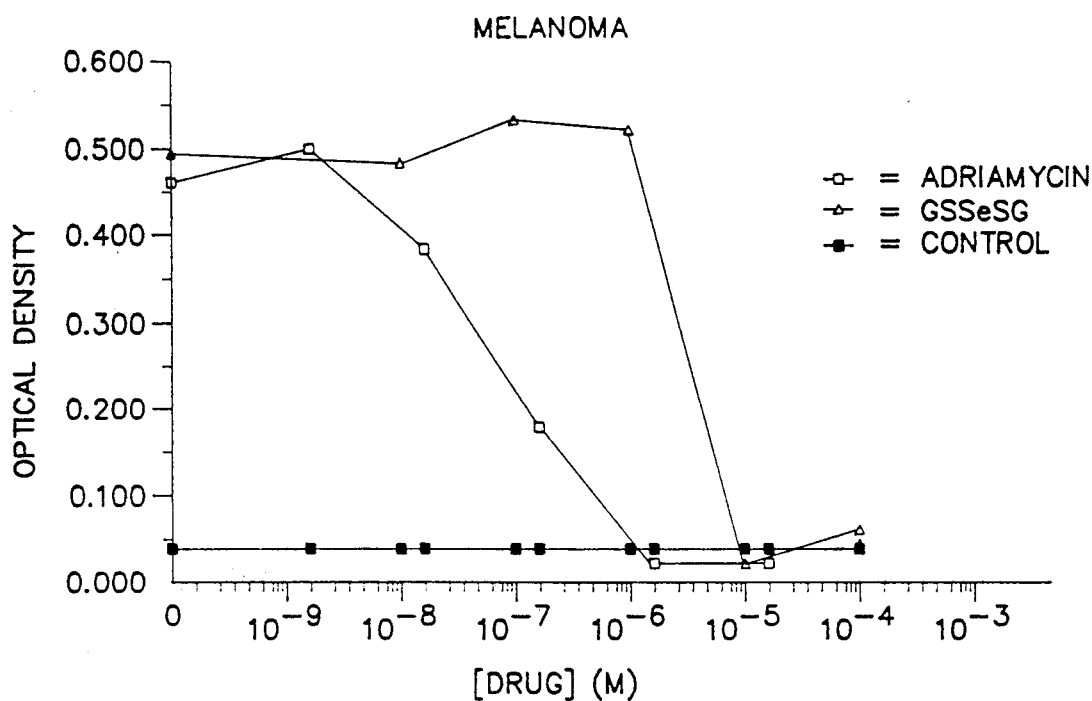
FIG. 6 provides a comparison of the effects at increasing concentrations of adriamycin and GSSeSG as measured by variations in optical density of the cell solution of melanoma.
Figure 7:
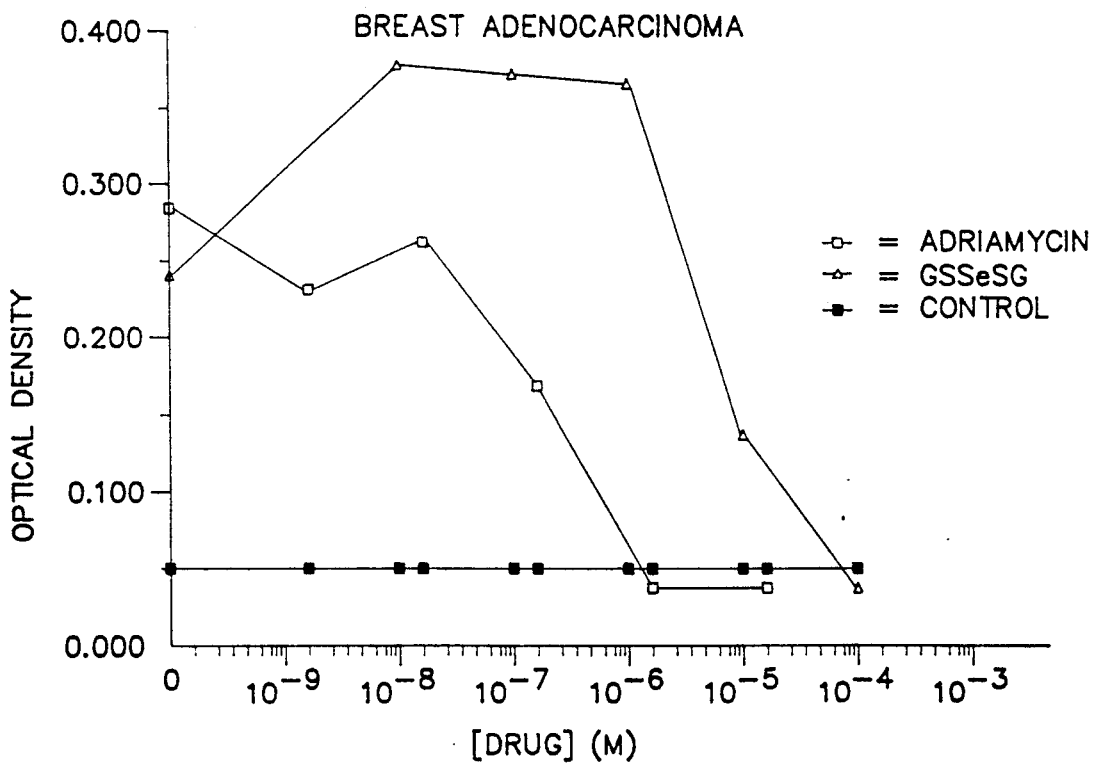
FIG. 7 provides a comparison of the effects at increasing concentrations of adriamycin and GSSeSG as measured by variations in optical density of the cell solution of breast adenocarcinoma.
Figure 8:
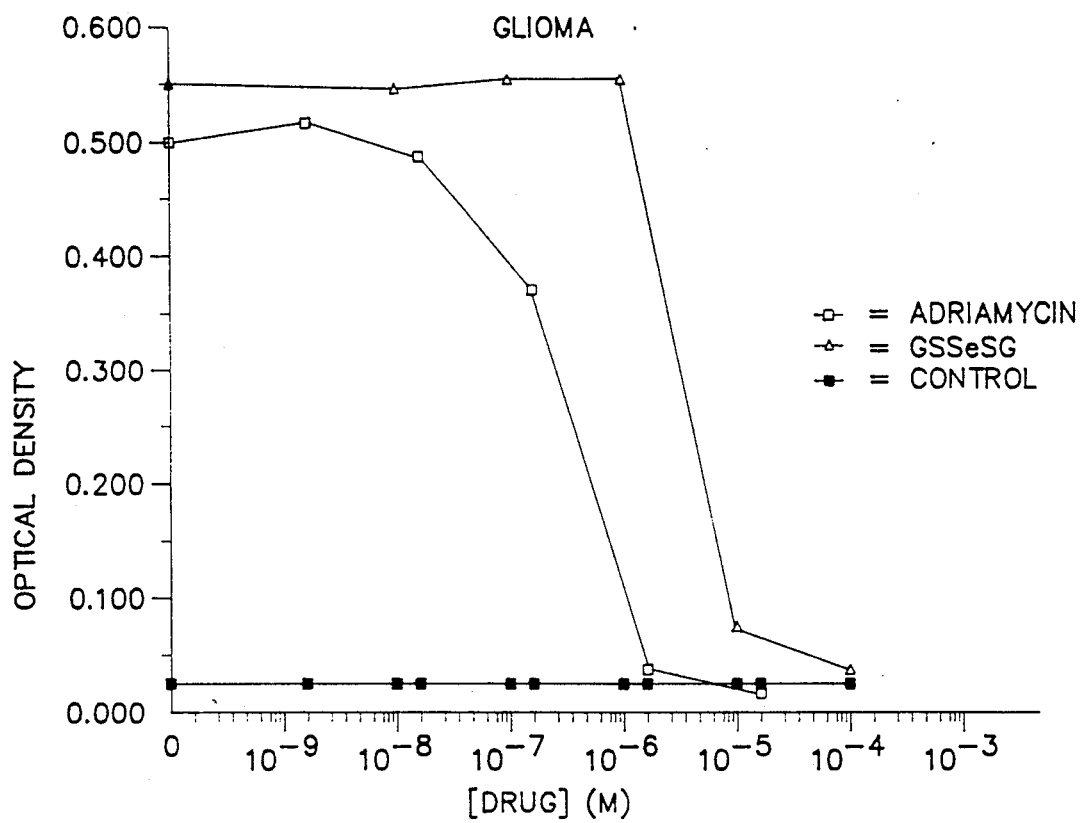
FIG. 8 provides a comparison of the effects at increasing concentrations of adriamycin and GSSeSG as measured by variations in optical density of the cell solution of glioma.
Figure 9:
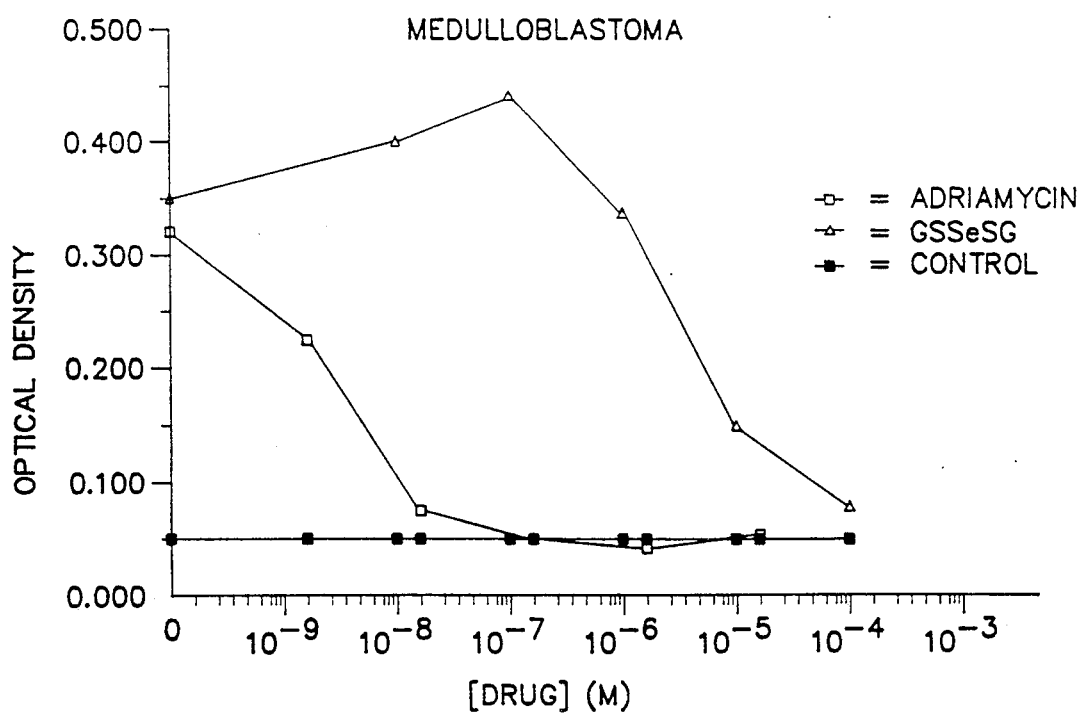
FIG. 9 provides a comparison of the effects at increasing concentrations of adriamycin and GSSeSG as measured by variations in optical density of the cell solution of medulloblastoma.
Figure 10:
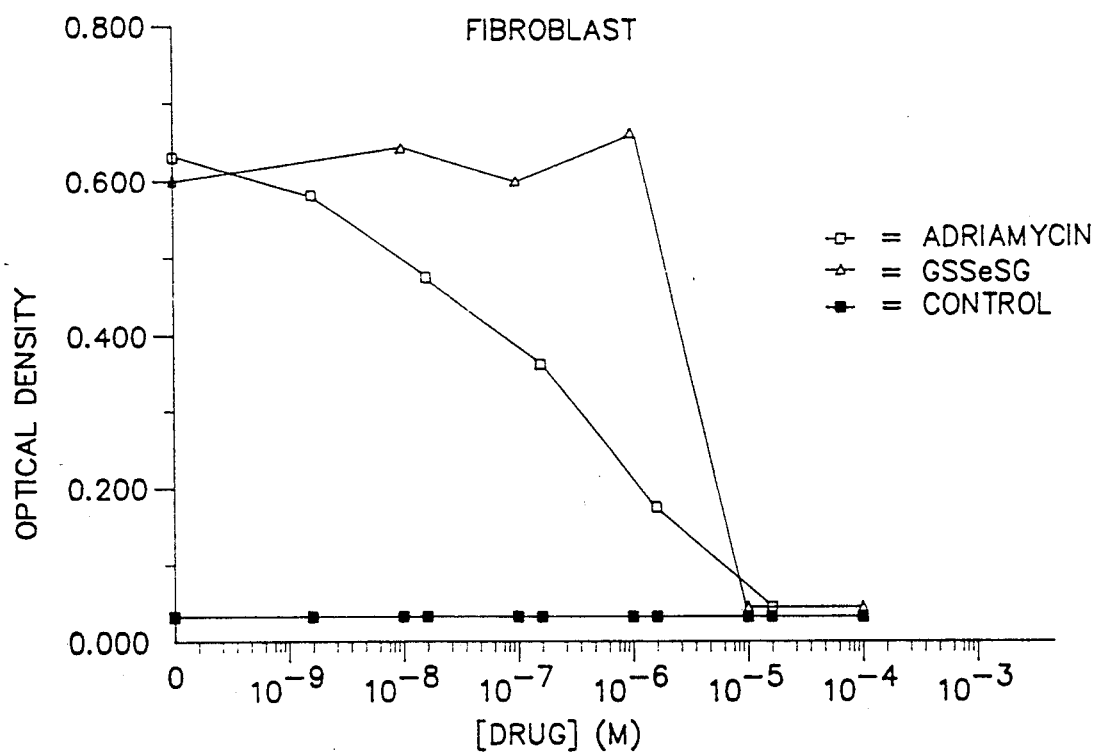
FIG. 10 provides a comparison of the effects at increasing concentrations of adriamycin and GSSeSG as measured by variations in optical density of the cell solution of fibroblast.
Figure 11:
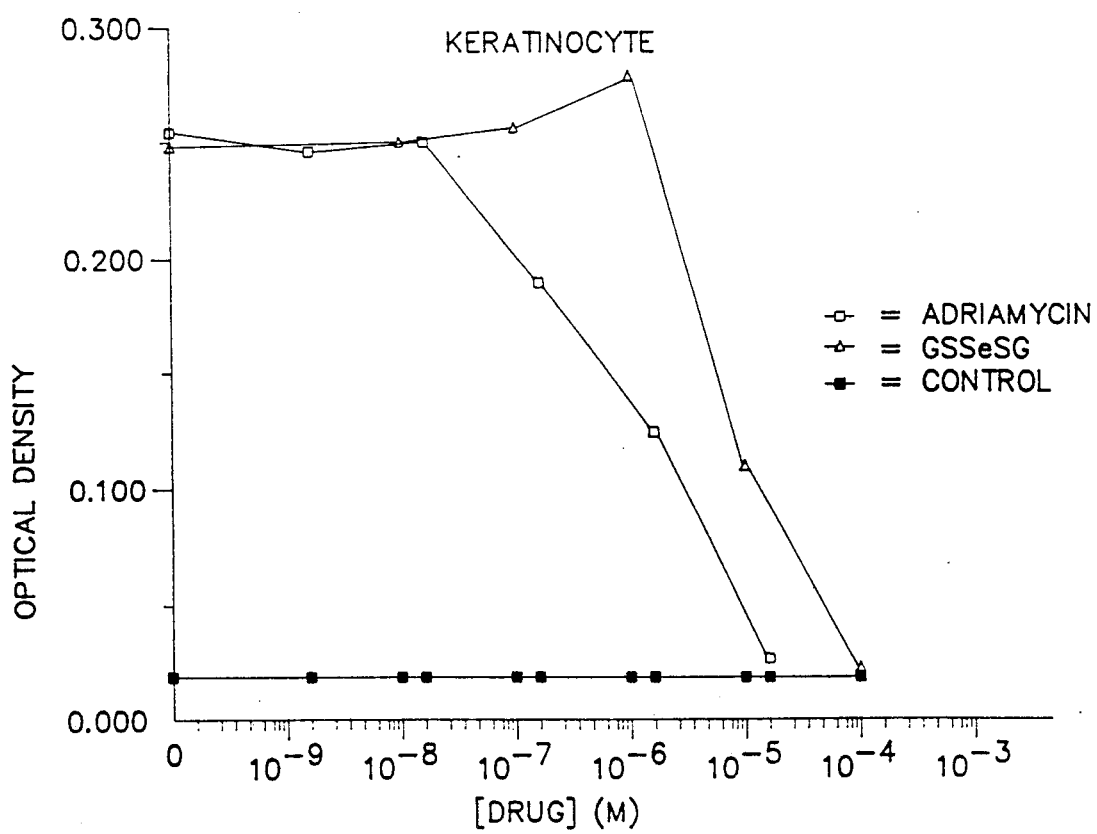
FIG. 11 provides a comparison of the effects at increasing concentrations of adriamycin and GSSeSG as measured by variations in optical density of the cell solution of keratinocyte.

FIG. 2 describes the effect that GSSeSG has with respect to the mutagenicity of 3 selenium containing, cancer treating agents as a function of their respective concentrations. More particularly, the preferred selenodithiol, GSSeSG, is contrasted with 2 other selenium containing compounds, selenite and selenomethionine in the treatment of peripheral blood lymphocytes, i.e., normal human cells drawn from the blood stream. The Figure discloses that the resulting low number of Sister Chromatid Exchanges, which are indicative of a low rate of inducible mutation after treatment with GSSeSG, indicates that the preferred selenodithiol is far less mutagenic than the other two anticarcinogens. As one in the art is aware, in the technique known as Sister Chromatid Exchange (SCE) the particular nucleotide components which comprise the DNA genetic code cross over to form cell mutations which lead to the birth and growth of rapidly dividing neoplastic cells.

Thus, the low number of SCE's which are induced by GSSeSG clearly indicates the decreased probability that non-neoplastic cells will spontaneously mutate in the presence of GSSeSG, thereby confirming that GSSeSG will not cause cancer itself.

Table 1, as seen in FIG. 3, illustrates the particular effectiveness of GSSeSG when administered in the crisis zone dosage range to a group of ten rats. The Table contrasts the results obtained by the desired dosage with the results obtained from four other groups of ten rats; the rats in each group being inoculated with cancer chemotherapeutics in differing dosages of both GSSeSG, retinol (HPR) and mixtures of each, as well as a control sample of fifty rats which were not administered with cancer treating agents. All one hundred rats were inoculated with DMBA (7,12-dimethylbenz(a)anthracene) so as to induce cancer cell formation, which was then allowed to form tumors over a period of two months prior to testing. It is seen that the control rats were fed a normal diet and had an average weight of 241 grams. One group of 10 rats were injected with 2 $\mu$g of GSSeSG per gram of bodyweight and presently all but one of these specimens are dead at seventy nine days. However cutting the GSSeSG concentration in half resulted in moving the effective concentration to the lower end of the aforementioned "crisis zone" range, thereby enabling GSSeSG to inhibit cancer cell proliferation within the rats without creating an accompanying toxicity to normal tissue (note the high body weights). Thus, the administration of GSSeSG at 1 microgram per gram of rat body weight not only resulted in the substantial elimination of the cancer cells but, as indicated by their bodyweight, resulted in substantially no harm to the rats. The other three groups of rats disclose the administration of GSSeSG mixed with the cancer treating agent retinol, as well as one test sample of just retinol, but while the anticarcinogens were effective in arresting the cancer. Thus, the Table clearly illustrates both the effectiveness of GSSeSG when utilized in the desired range of proportions, while the proper range of dosages is substantially non toxic to the treated host.

It has further been discovered that the injection of rats with effective dosages of GSSeSG at a site distant from the tumor will still kill the cancer tumors. This was demonstrated by the disappearance of the superficial tumors that were located a distance from the point of injection of GSSeSG.

Thus by the process of the present invention selenodithiol and particularly GSSeSG can effectively inhibit tumor cell proliferation in both humans and animals. Rats displaying various size tumors were treated by injection or cannulation of GSSeSG directly into the tumor, generally at a site on the tumor which was proximal to the body so as to have the GSSeSG drawn into the tumor by the circulation. In this manner, the GSSeSG is caused to radiate outwardly from the site of injection or cannulation into the tumor mass according to the law of diffusion based on the inverse square. Thus an amount of GSSeSG which is a toxic level at the local site of injection or cannulation is administered and, after radiating outwardly is reduced in concentration to not only a safe level, but in fact, is reduced to a level which stimulates cell growth or proliferation. A rapid acceleration of the proliferation of cells located peripherally and at a certain distance from the site of injection or cannulation is thus observed. These cells can be cancer cells or non-cancer cells. This is a result of the surprising biphasic effect of the present invention. Thus a method is provided for accelerating the growth of non-cancerous cells surrounding a cancer tumor, or the production of cancer cell lines, such as for culture media purposes.

Repeated injections over a period of time are generally required to achieve the desired reduction in tumor size. As a result of the biphasic effect, initially the tumor may actually grow in size depending on the concentration of selenodithiol administered. However, with repeated injections or cannulation of the selenodithiol to the tumor, a toxic level is eventually attained resulting in the reduction or death of the tumor.

It is not clear how the selenodithiol functions within the tumor to so effectively reduce or eliminate the tumor. It is believed, but the inventors do not wish to be limited to the theory, that the selenodithiol may be killing endothelial cells supporting the vascular cell walls of the blood vessels feeding the tumor. By destroying the cells which support the vascular system feeding the tumor, the tumor is starved from its blood supply and shrinks or dies. In addition, it is believed that the selenodithiol is effective in the direct killing of tumor cells themselves.

The compounds of this invention will generally be administered to animals, including but not limited to, mammals including humans. In the broadest embodiment, it is believed that any cell containing EF-2 can be inhibited by GSSeSG administered at levels of $10^{-6}$M to $10^{-5}$M, and any cell containing EF-2 can be stimulated to grow by the GSSeSG administered at levels of $10^{-8}$M to $10^{-6}$M ; thus, the compositions of the invention are effective in all eucaryotic cells, including but not limited to, mammalian neoplasms and chemically induced as well as naturally induced cancerous cells.

Additionally, it is believed that the active compounds of this invention can be processed in accordance with conventional methods of galenic pharmacy to produce appropriate medicinal agents for administration to the desired host patient.

The compounds of this invention can be employed in a mixture with conventional excipients, i.e. pharmaceutically acceptable, organic or inorganic carrier substances suitable for parenteral, nasal, transdermal or oral application which do not deleteriously react with the active compounds. Suitable pharmaceutically acceptable carriers include, but are not limited to water, salt solutions, alcohols, gum arabic, vegetable oils, benzyl alcohols, polyethylene glycose, gelatine, carbohydrates such as lactose, amylose, or starch, magnesium stearate, talc, silicic acid, viscous paraffin, perfume oil, fatty acid monoglycerides, and diglycerides, pentaerythritol fatty acids esters, hydroxy methyl-cellulose, pyrrolidone, etc. The resultant preparations can be sterilized and, if desired, mixed with an auxiliary agent, e.g. lubricants, preservatives, stabilizers, wetting agents, emulsifiers, salts for influencing osmotic pressure, buffers, coloring, flavoring and/or aromatic substances and the like which do not deleteriously react with the active compounds. They can also be combined or desired with other active agents, e.g. vitamins.

For parenteral application, particularly suitable are injectable sterile solutions, preferably oily or acquiesce solutions, as well as suspensions, emulsions or implants, including suppositories.

For oral application, particularly suitable are tablets, dragees, liquids, drops, suppositories, or capsules. A syrup, elixir, or the like can be used wherein a sweetened vehicle is employed.

Sustained or directed release compositions can be formulated, e.g. liposomes were those wherein the active ingredient is protected with differentially degradable coatings, e.g. by microencapsulation, multiple coatings, etc.

Although it has been indicated above that a particularly narrow concentration range is not only preferred, but essential, it should also be appreciated that the actual preferred amounts of active compound in a specific case can vary according to the specific compound being utilized, the particular composition formulated, the mode of application, and the particular size and organisms or tumors being treated. Dosages for given host can be determined using conventional considerations, e.g., by customary comparison of the differential activities of the subject compound and of a known agent.

To measure the effect of GSSeSG on cellular activity as a function of concentration the microculture tetrazolium assay (MTA) technique was employed. (See Mosmann, T., *J. Immun. Meth.*, 1983, 65, 55-63) This technique measures the effectiveness of experimental chemotherapeutic agents on various human tumor cell lines. Mitochondrial enzymes of active tumor cells have the capacity to reduce a yellow tetrazolium solution to a blue formazan product. Variations in optical density, measured by a spectrophotometer, are indicative of the level of cellular activity. FIGS. 4 through 11 show the results of GSSeSG compared to adriamycin at varying concentrations on reducing the level of cellular activity. The results of these Figs. demonstrate that all cell lines responded to GSSeSG in a biphasic manner, i.e., concentrations from $10^{-8}$ Molar to $10^{-6}$ Molar, activity was enhanced and between $10^{-6}$ Molar and $10^{-5}$ Molar, activity was significantly inhibited, indicating cytoxic levels.

Figure 12:
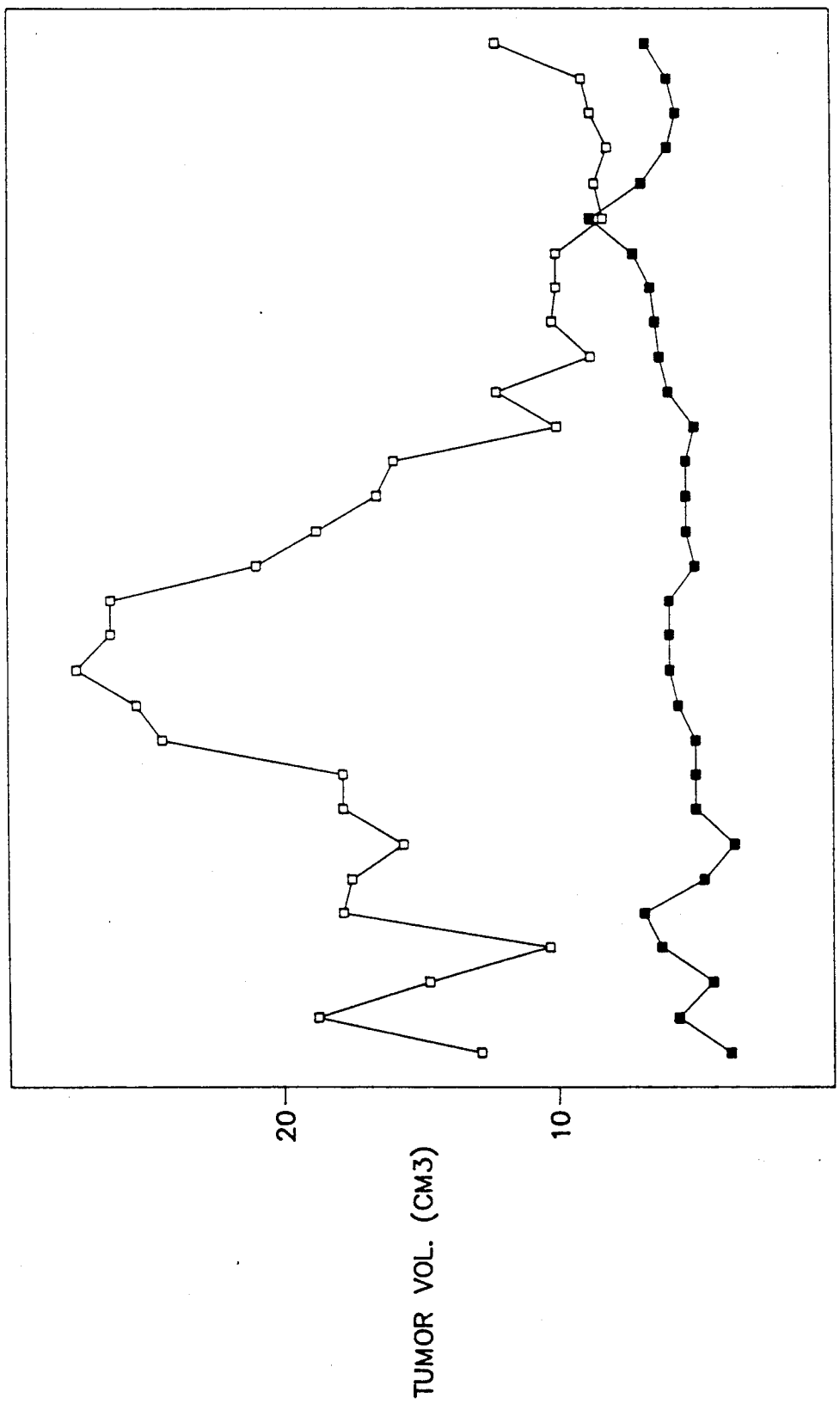
FIG. 12 shows the effect of selenodiglutathione on the reduction of the size of rat mammary tumor when injected directly into the tumor.

In another example of the present invention, the effect of selenodiglutathione on rat mammary tumor is shown in FIG. 12. The tumor was induced in each rat by the administration of 7,12-dimethylbenz(a)anthracene and allowed to proliferate to a pre-determined size range. The selenodiglutathione was injected at a level of 700 micrograms directly into the tumor mass 15 times over the course of 30 days. FIG. 12 presents the volume changes of the tumors. The tumors so injected exhibited a significant regression in volume, indicative of the toxic effect of the selenodiglutathione on the cancer cells in the tumors. This demonstrates an effective reduction in the size of the tumor without any detrimental effect to the animal itself. The treatment schedule resulted in growth regression of a large range of tumor sizes but was originally calculated as the optimal dose for the ablation of a tumor 1 centimeter of average diameter, where average diameter is the average of the major and minor axes of the ellipsoid tumor. Injections of 1400 micrograms 8 times over the course of 30 days provided a much more erratic reduction in tumor size and to a lesser extent. Thus a dose range of from 0.5 micrograms of GSSeSG per milligram of tumor to 5.0 micrograms per milligram of tumor is preferred and will produce regression at the low end and ablation at the high end.

From the foregoing description, one skilled in the art can easily ascertain the essential characteristics of this invention, and without departing from the spirit and scope thereof, can make various changes and modifications of the invention to adapt it to various usages and conditions.

While certain preferred embodiments of the present invention have been disclosed in detail, it is to be understood that various modifications may be adopted without departing from the spirit of the invention or scope of the following claims.

We claim:

1. A biphasic method for the treatment of eucaryotic cells containing the elongation factor 2 (EF-2) comprising in a first phase the administration to the cells of a selenodithiol compound at a level of from $10^{-6}$M to $10^{-5}$M, whereby the EF-2 is inhibited, and in a second phase, the administration to the cells of a selenodithiol compound at a level of from $10^{-8}$M to $10^{-6}$M, whereby the EF-2 is stimulated.

2. The method of claim 1 wherein the selenodithiol compound is selected from the group consisting of selenodimethionine, selenodicysteine, and selenodiglutathione.

* * * * *